United States Patent
Kim et al.

(10) Patent No.: US 10,800,824 B2
(45) Date of Patent: Oct. 13, 2020

(54) AIMP1 PROTEIN FRAGMENT AND SKIN-PROTECTING COMPOSITION CONTAINING SAME AS ACTIVE INGREDIENT

(71) Applicant: NEOMICS CO., LTD., Seoul (KR)

(72) Inventors: Sunghoon Kim, Seoul (KR); Min Chul Park, Gyeonggi-do (KR)

(73) Assignee: NEOMICS CO., LTD., Seoul (KR)

( * ) Notice: Subject to any disclaimer, the term of this patent is extended or adjusted under 35 U.S.C. 154(b) by 0 days.

(21) Appl. No.: 16/320,431

(22) PCT Filed: Jul. 27, 2017

(86) PCT No.: PCT/KR2017/008077
§ 371 (c)(1),
(2) Date: Jan. 24, 2019

(87) PCT Pub. No.: WO2018/021838
PCT Pub. Date: Feb. 1, 2018

(65) Prior Publication Data
US 2020/0010524 A1 Jan. 9, 2020

(30) Foreign Application Priority Data

Jul. 28, 2016 (KR) .................... 10-2016-0096240

(51) Int. Cl.
| | |
|---|---|
| *A61K 8/64* | (2006.01) |
| *A61K 38/10* | (2006.01) |
| *C07K 7/08* | (2006.01) |
| *C07K 14/47* | (2006.01) |
| *C07K 14/52* | (2006.01) |
| *A61Q 19/00* | (2006.01) |
| *A23L 33/18* | (2016.01) |
| *A61Q 19/08* | (2006.01) |

(52) U.S. Cl.
CPC .............. *C07K 14/52* (2013.01); *A23L 33/18* (2016.08); *A61K 8/64* (2013.01); *A61Q 19/08* (2013.01); *A23V 2002/00* (2013.01)

(58) Field of Classification Search
CPC . A61K 8/64; A61K 38/10; C07K 7/08; C07K 14/47; C07K 14/52; A61Q 19/00; A23L 33/18
USPC ...... 514/1.1, 18.8, 21.4, 21.5; 530/300, 326, 530/327
See application file for complete search history.

(56) References Cited

U.S. PATENT DOCUMENTS

2009/0305973 A1* 12/2009 Kim ................ C07K 14/47
514/20.1

FOREIGN PATENT DOCUMENTS

| KR | 10-2007-0100329 A | 10/2007 |
| KR | 10-1020658 B1 | 3/2011 |
| WO | WO 2006/083087 A1 | 8/2006 |

OTHER PUBLICATIONS

D6R937 from UniProt, pp. 1-5. Integrated into UniProtKB/TrEMBL Jul. 13, 2010. (Year: 2010).*
A0A286XYL6 from UniProt, pp. 1-4. Integrated into UniProtKB/TrEMBL Nov. 22, 2017. (Year: 2017).*
Pearson WR., "An Introduction to Sequence Similarity ("Homology") Searching," Current Protocols in Bioinformatics, 3.1.1-3.1.8. (Year: 2013).*
Kanduc D, "Homology, similarity, and identity in peptide epitope innnnunodefinition," Journal of Peptide Science, 18: 487-794. (Year: 2012).*
International Search Report in corresponding PCT Application No. PCT/KR2017/008077, dated Nov. 9, 2017.
"Get Rid of Wrinkles and Keep Your Skin Resilient Through Our Elasticity Care at TATOA Clinic, the Dermatologit's Office at SINSA Station!", Naer Blog.~Beauty Wonder Drug~ [online]. Posted on Jun. 5, 2014, Internet: <http://blog.naver.com/tatoa0222/220021300454>.
Park. Sang Gyu et al., "Aminoacyl-tRNA Synthetase-interacting Multifunctional Proteins (AIMPs): A Triad for Cellular Homeostasis," IUBMB Life, Apr. 2010, vol. 62, No. 4, pp. 296-302.
Kim, Seo Yoon et al., "ARS-interacting Multi-functional Protein 1 Induces Proliferation of Human Bone Marrow-derived Mesenchymal Stem Cells by Accumulation of B-catenin via Fibroblast Growth Factor Receptor 2-mediated Activation of Akt" Stem Cells and DevelOpment, May 14, 2013 (online), vol. 22, No. 19, pp. 2630-2640.
Extended European Search Report in corresponding European Application No. EP 1783 4779, dated Dec. 12, 2019.

* cited by examiner

*Primary Examiner* — Julie Ha
(74) *Attorney, Agent, or Firm* — Leason Ellis LLP

(57) ABSTRACT

Fragments of ARS-interacting multi-functional protein 1 (AIMP1) protein and a composition comprising the same as an active ingredient for preventing skin-aging, anti-wrinkle, and improving skin flexibility or elasticity are described.

11 Claims, 4 Drawing Sheets

Specification includes a Sequence Listing.

AIMP1 PROTEIN FRAGMENT AND SKIN-PROTECTING COMPOSITION CONTAINING SAME AS ACTIVE INGREDIENT

CROSS-REFERENCE TO RELATED PATENT APPLICATIONS

This application is a U.S. National Phase Application under 35 U.S.C. § 371 of International Patent Application No. PCT/KR2017/008077, filed Jul. 27, 2017, and claims priority to KR 10-2016-0096240, filed Jul. 28, 2016, all of which are incorporated by reference in their entireties. The International Application was published on Feb. 1, 2018 as International Publication No. WO/2018/021838 A1.

SEQUENCE LISTING

The instant application contains a Sequence Listing which has been submitted electronically in ASCII format and is hereby incorporated by reference in its entirety. Said ASCII copy, created on Jan. 24, 2019, is named 10524_007399_US0_SEQLST.txt and is 15 kilobytes in size.

TECHNICAL FIELD

The present application claims priority from and the benefit of Korean Patent Application No. 10-2016-0096240 filed on Jul. 28, 2016, which is hereby incorporated by reference for all purposes as if fully set forth herein.

The present invention relates to novel fragments of AIMP1 protein and a composition comprising the same as an active ingredient for preventing skin-aging, anti-wrinkle, and improving skin flexibility or elasticity, more specifically it relates to a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide; a polynucleotide encoding the polypeptide; a composition for anti-wrinkle, preventing skin-aging, improving skin flexibility and elasticity comprising the polypeptide as an active ingredient.

BACKGROUND ART

The pharmaceutical industry is changing from the development of natural products or chemical synthetic medications in the past to the development of protein or peptide drugs. Protein is the basic substance in the function and structure of life, and it is estimated that the protein constituting the human body is more than one million. It has been directly related to diseases and has become an important research subject for the development of therapeutic drugs. Protein or peptide drugs using them have been evaluated as innovations in pharmaceuticals because they have fewer side effects and are more effective than synthetic drugs. Currently, the importance of biomedicines in the pipeline of major pharmaceutical companies is increasing, but there are major technical problems until the launch of certain biomedicines such as peptides. Specifically, improvement of delivery technique, development of peptide with increased stability and half-life, and long-chain peptide synthesis are obstacles to commercialization. Peptides are made up of about 50 amino acids or less. It is known that to be successful as a peptide drug, it is important to find a peptide having short sequence and activity. If the peptide length is long, the synthesis cost is high and the production is not easy, and it is known that there is an absorption problem in human body.

Human skin consists of two layers of epidermis and dermis. The epidermis is the thinnest layer located at the outermost part of the skin and plays an important role in moisturizing and protecting the skin. More specifically, the epidermis prevents substances in our body from escaping from the body, and prevents entry of harmful substances such as ultraviolet rays, viruses, and bacteria that enter from the outside. In addition, the epidermis naturally emulsifies the sebaceous glands and sweat glands water to form weakly acidic sebum, protects against harmful substances, and sterilizes bacteria.

The dermis in the skin nourishes the epidermis, supports the epidermis, protects the body from external damage, functions to store moisture, and regulates body temperature. The dermis is composed of fibroblast and its extracellular matrix, and it contains nerve, blood vessels, lymphatic vessels, muscle and sebaceous glands, skin appendages such as apocrine and eccrine glands. Fibroblasts, a major component of the dermis, synthesize extracellular matrix such as collagen, proteoglycans and other structural glycoproteins. Among them, collagen is a fiber protein that occupies 70% of the dermis, and functions as the mechanical firmness (elasticity) of the skin, the resistant force of the connective tissue and the binding force of the tissue, the support of cell adhesion, and induces cell division and proliferation (Van der M. Rest et al., Biometerials., 11:28-31, 1990; Shimokomaki M. et al., Ann. N. Y. Acad. Sci., 580:1-7, 1990; Van der Rest M. et al., Biochimie., 72(6-7):473-484, 1990).

There are various physical and chemical changes in human skin through aging process. The skin-aging is divided into 2 types according to causes, an intrinsic aging that is a natural aging phenomenon in which the structure and physiological functions of the skin continuously deteriorate with aging, and an extrinsic aging that is caused by external factors such as ultraviolet rays, side effects of drugs or environmental factors. As human skin passes through the aging process, cellular components (such as lipids in cell membranes) are oxidized by reactive oxygen species produced by the metabolism of skin cells or ultraviolet rays, and their activity and biosynthesis are inhibited. Thus, as the skin ages, the skin becomes thinner as a whole, the skin becomes dehydrated and dry, and fine wrinkles are generated more and the wrinkles gradually become deeper. In addition, the amount of collagen that occupies most of the dermis is decreased, and the activity of the fibroblast that synthesizes collagen is also decreased, so that the synthesis of new collagen is also reduced. As the amount of collagen in the dermis decreases, the thickness of the dermis also decreases, resulting in wrinkles on the skin and poor flexibility and elasticity. Therefore, by stimulating collagen metabolism by promoting fibroblast proliferation and collagen synthesis in the skin, there is a continuing increase in demand for safe skin materials with less side effects and excellent effect on anti-wrinkle, improving flexibility and elasticity, and preventing skin-aging Meanwhile, ARS-interacting multi-functional protein 1 (AIMP1) is a protein consisting of 312 amino acids, and binds to a multi-tRNA synthetase complex, so that increases catalytic activity of the multi-tRNA synthetase complex. With respect to the activity of the AIMP1 protein, the inventors of the present invention have found that the 6th to 46th amino acid region of the AIMP1 protein have an activity of promoting collagen synthesis (refer to Korean Patent Registration No. 10-0903984, Jun. 15, 2009). However, active sites showing effect on increasing collagen synthesis and fibroblast proliferation in the 6th to 46th amino acid region of the AIMP1 protein have not yet been investigated.

DETAILED DESCRIPTION OF THE INVENTION

Technical Problem

Accordingly, the present inventors have confirmed that 6th to 46th amino acid region of the AIMP1 protein substantially shows effect on preventing skin-aging, anti-wrinkle, and improving skin flexibility and elasticity, thereby completing the present invention.

Therefore, an aspect of the present invention is to provide a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide.

Another aspect of the present invention is to provide a polypeptide consists of amino acid sequence of SEQ ID NO: 2 or SEQ ID NO: 3, or a polypeptide consisting of an amino acid sequence having 70% or more sequence homology with the polypeptide.

Another aspect of the present invention is to provide a polynucleotide encoding the polypeptide.

Another aspect of the present invention is to provide a cosmetic composition for anti-wrinkle, improving skin flexibility and elasticity, the composition comprising as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide.

It is also to provide a cosmetic composition for anti-wrinkle, improving skin flexibility and elasticity, the composition consisting of as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide.

It is also to provide a cosmetic composition for anti-wrinkle, improving skin flexibility and elasticity, the composition consisting of as an active ingredient a polypeptide consisting essentially of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide.

Another aspect of the present invention is to provide a food composition for anti-wrinkle, improving skin flexibility and elasticity, the composition comprising as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide.

It is also to provide a food composition for anti-wrinkle, improving skin flexibility and elasticity, the composition consisting of as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide.

It is also to provide a food composition for anti-wrinkle, improving skin flexibility and elasticity, the composition consisting of as an active ingredient a polypeptide consisting essentially of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide.

Another aspect of the present invention is to provide a cosmetic composition for preventing skin-aging, the composition comprising as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide.

It is also to provide a cosmetic composition for preventing skin-aging, the composition consisting of as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide.

It is also to provide a cosmetic composition for preventing skin-aging, the composition consisting essentially of as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide.

Another aspect of the present invention is to provide a food composition for preventing skin-aging, the composition comprising as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide.

It is also to provide a food composition for preventing skin-aging, the composition consisting of as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide.

It is also to provide a food composition for preventing skin-aging, the composition consisting essentially of as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide.

Another aspect of the present invention is to provide use of the polypeptide for preparing an agent for anti-wrinkle, improving skin flexibility and elasticity.

Another aspect of the present invention is to provide a method for anti-wrinkle, improving skin flexibility and elasticity, the method comprising administering to a subject in need thereof an effective amount of the polypeptide.

Another aspect of the present invention is to provide use of the polypeptide for preparing an agent for preventing skin-aging.

Another aspect of the present invention is to provide a method for preventing skin-aging, the method comprising administering to a subject in need thereof an effective amount of the polypeptide.

Technical Solution

Therefore, in accordance with an aspect of the present invention, there is provided a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide.

In accordance with an aspect of the present invention, there is provided a polypeptide consists of amino acid sequence of SEQ ID NO: 2 or SEQ ID NO: 3, or a polypeptide consisting of an amino acid sequence having 70% or more sequence homology with the polypeptide.

In accordance with an aspect of the present invention, there is provided a polynucleotide encoding the polypeptide.

In accordance with an aspect of the present invention, there is provided a cosmetic composition for anti-wrinkle, improving skin flexibility and elasticity, the composition comprising as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide.

The present invention also provides a cosmetic composition for anti-wrinkle, improving skin flexibility and elasticity, the composition consisting of as an active ingredient a polypeptide consisting of 4 to 17 consecutive amino acids from the amino acid sequence of SEQ ID NO: 1, wherein the polypeptide comprises the amino acids KGAE of SEQ ID NO: 1), or a polypeptide consisting of an amino acid sequence having 70% or more sequence homology with the polypeptide.

The present invention also provides a cosmetic composition for anti-wrinkle, improving skin flexibility and elasticity, the composition consisting of as an active ingredient a polypeptide consisting essentially of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide.

In accordance with an aspect of the present invention, there is provided a food composition for anti-wrinkle, improving skin flexibility and elasticity, the composition comprising as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1, or a polypeptide consisting of an amino acid sequence having 70% or more sequence homology with the polypeptide.

The present invention also provides a food composition for anti-wrinkle, improving skin flexibility and elasticity, the composition consisting of as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide.

The present invention also provides a food composition for anti-wrinkle, improving skin flexibility and elasticity, the composition consisting essentially of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide.

In accordance with an aspect of the present invention, there is provided a cosmetic composition for preventing skin-aging, the composition comprising as an active ingredient a polypeptide consisting of 4 to 17 consecutive amino acids from the amino acid sequence of SEQ ID NO: 1, wherein the polypeptide comprises the amino acids residue KGAE (residues 9 to 12 of SEQ ID NO: 1), or a polypeptide consisting of an amino acid sequence having 70% or more sequence homology with the polypeptide.

The present invention also provides a cosmetic composition for preventing skin-aging, the composition consisting of as an active ingredient a polypeptide consisting of 4 to 17 consecutive amino acids from the amino acid sequence of SEQ ID NO: 1, wherein the polypeptide comprises the amino acids KGAE (residues 9 to 12 of amino acid sequence of SEQ ID NO: 1), or a polypeptide consisting of an amino acid sequence having 70% or more sequence homology with the polypeptide.

The present invention also provides a cosmetic composition for preventing skin-aging, the composition consisting essentially of as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide.

In accordance with an aspect of the present invention, there is provided a food composition for preventing skin-aging, the composition comprising as an active ingredient a polypeptide consisting of 4 to 17 consecutive amino acids from the amino acid sequence of SEQ ID NO: 1, the polypeptide comprises the amino acids KGAE (residues 9 to 12 of SEQ ID NO: 1), or a polypeptide consisting of an amino acid sequence having 70% or more sequence homology with the polypeptide.

The present invention also provides a food composition for preventing skin-aging, the composition consisting of as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide.

The present invention also provides a food composition for preventing skin-aging, the composition consisting essentially of as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide.

In accordance with an aspect of the present invention, there is provided use of the polypeptide for preparing an agent for anti-wrinkle, improving skin flexibility and elasticity.

In accordance with an aspect of the present invention, there is provided a method for anti-wrinkle, improving skin flexibility and elasticity, the method comprising administering to a subject in need thereof an effective amount of the polypeptide.

In accordance with an aspect of the present invention, there is provided use of the polypeptide for preparing an agent for preventing skin-aging.

In accordance with an aspect of the present invention, there is provided a method for preventing skin-aging, the method comprising administering to a subject in need thereof an effective amount of the polypeptide.

Hereinafter, the present invention will be described in detail.

The term "KGAE residue", "KGAE sequence", or "KGAE region" in the present invention can be used interchangeably and refers to the 14th to 17th amino acid region in the full length amino acid sequence of AIMP1 protein represented by SEQ ID NO: 5 (residues 14 to 17 of SEQ ID NO: 5). And the region corresponds to the 9th to 12th amino acid residues in the polypeptide of SEQ ID NO: 1 (residues 9 to 12 of SEQ ID NO: 1) (or referred to as "Neo-Pep") which is the example of the skin protecting fragment provided by the present invention.

Hereinafter, the polypeptide provided by the present invention is a fragment derived from AIMP1 protein, which comprises the amino acids KGAE (residues 9 to 12 of SEQ ID NO: 1) and has remarkably excellent effect on anti-wrinkle, promoting skin flexibility and elasticity, and preventing skin-aging. It is disclosed in the present invention for the first time that the KGAE region of AIMP1 is essential for anti-wrinkle, promoting skin flexibility and elasticity, and preventing skin-aging.

Therefore, the present invention provides a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide. Preferably, the polypeptide consists of 10 to 15 consecutive amino acids.

Preferably, the polypeptide of the present invention is a polypeptide consisting of an amino acid sequence of SEQ ID NO: 2 or SEQ ID NO: 3, or a polypeptide consisting of an amino acid sequence having 70% or more sequence homology with the polypeptide.

As used herein, the terms "polypeptide", "peptide" and "protein" are used interchangeably and refer to polymers of amino acid residues as commonly found in natural state proteins.

The one letter (triplet) of amino acids used herein means the following amino acids according to standard abbreviations in the biochemistry: A (Ala): alanine; C (Cys): cysteine; D (Asp): aspartic acid; E (Glu): glutamic acid; F (Phe): phenylalanine; G (Gly): glycine; H (His): histidine; I (Ile): isoleucine; K (Lys): lysine; L (Leu): leucine; M (Met): methionine; N (Asn): Asparagine; O (Ply): pyrrolysine; P (Pro): proline; Q (Gln): Glutamine; R (Arg): arginine; S (Ser): serine; T (Thr): threonine; U (Sec): selenocysteine, V (Val): valine; W (Trp): tryptophan; Y (Tyr): Tyrosine.

In the present invention, 'AIMP1 (ARS-interacting multi-functional protein 1) protein' was firstly known as p43 protein and was renamed as AIMP1 (Kim S H et al., Trends in Biochemical Sciences, 30: 569-574, 2005). AIMP1 binds to a multi-tRNA synthetase complex to enhance the catalytic activity of the multi-tRNA synthetase.

The specific sequence of the AIMP1 protein of the present invention is not particularly limited as long as it is known in the art and can be preferably human AIMP1. Three SNPs of the AIMP1 protein are known (see NCBI SNP database): 79th alanine (Ala) in the amino acid sequence of the full-length AIMP1 (SEQ ID NO: 7 in the present specification) is substituted with proline (Pro) (SNP Accession No. rs3133166, SEQ ID NO: 11); 104th threonine (Thr) is substituted with alanine (Ala) (SNP Accession No. rs17036670, SEQ ID NO: 12); 117th threonine (Thr) is substituted with alanine (Ala) (SNP Accession No. rs2230255, SEQ ID NO: 13).

The polypeptide of the present invention, that is, polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), include functional equivalent thereof. The functional equivalent means a polypeptide having at least 70% or more (70.0% to 99.9%), preferably 80% or more (80.0% to 99.9%), and more preferably 90% or more (90% to 99.9%) sequence homology (or identity) with the polypeptide of the present invention. More preferably, the functional equivalent means polypeptide having at least 70% or more, preferably 80% or more, and more preferably 90% or more sequence homology (or identity) with the polypeptide of the present invention with constant (unchanged) sequence of KGAE region (residues 9 to 12 of SEQ ID NO: 1 or residues 14 to 17 of SEQ ID NO: 5). For example, these include polypeptides having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence homology, and exhibits substantially the same physiological activity as the polypeptide of the present invention. Herein, the term "substantially" means a state indicating a property of a certain property to a whole or almost the same degree. Therefore, in the present invention, "substantially the same physiological activity" means activity of preventing skin-aging, anti-wrinkle, and improving skin flexibility and elasticity through the effect on promoting collagen synthesis and/or proliferation of fibroblast.

In the present invention, "homology or identity" refers to the overall relatedness between polymer molecules, such as polypeptide molecules. For example, calculation of homology/identity (%) between two polypeptide sequences can be performed by aligning two sequences for optimal comparison. Preferably, the length of the sequence arranged for comparison purposes is at least 30%, at least 40%, at least 50%, at least 60%, at least 70%, at least 80% %, at least 90%, or substantially 100% of the reference sequence. Then, the amino acids at the corresponding amino acid sites are compared with each other. If the amino acid located at the first sequence is identical to the amino acid at the corresponding site of the second sequence, the two sequences are identical at that site. The identity (%) of the two sequences is a function of the number of sites having amino acids common to the two sequences, taking into account the number and length of the gaps to be introduced for optimal alignment between the two sequences. The comparison between two sequences and the determination of identity (%) can be performed through a mathematical algorithm. For example, ClustalW (Thompson et al., 1994) can be used to measure sequence identity values using the following parameters: Pair Array Parameters—Method: Accurate, Matrix: PAM, Gap open penalty: 10.00, Gap extension penalty: 0.10; Multiple array parameters—Matrix: PAM, Gap open penalty: 10.00, delay identity: 30, penalize end gaps: on, Gap separation distance: 0, Negative Matrix: no, gap extension penalty: 0.20, residue-specific gap penalties: on, hydrophilic gap penalty: on, hydrophilic residue: GPSNDQEKR. Sequence identity in a particular residue includes the same residue that is simply derivatized.

In the present invention, the term "substantially" means a state indicating a property of a certain property to a whole or almost the same degree. The term "substantially the same" in the present invention is used related to the comparison between amino acid or nucleic acid sequences. For those of ordinary skill in the art to which the present invention pertains, two sequences will be understood to be "substantially identical" if they have identical residues at corresponding sites. As is well known in the art, amino acid or nucleic acid sequences can be compared using a variety of algorithms, for example, computer programs such as BLASTN for nucleic acid sequence comparison, BLASTP, gapped BLAST or PSI-BLAST for amino acid sequence comparison can be used. Examples of such computer programs are described in the following references: Altschul et al., Basic local alignment search tool, J. Mol. Biol., 215(3): 403-410, 1990; Altschul et al., Methods in Enzymology; Altschul et al., Nucleic Acids Res. 25:3389-3402, 1997; Baxevanis 외, Bioinformatics: A Practical Guide to the Analysis of Genes and Proteins, Wiley, 1998; 및 Misener et al., (eds.), Bioinformatics Methods and Protocols (Methods in Molecular Biology, Vol. 132), Humana Press, 1999. In addition to searching for the same sequence, the computer programs described above typically provide a degree of identity. In two sequences, it is considered to be "substantially the same" sequences if at least 70%, preferably at least 80%, at least 85%, at least 90%, at least 91%, at least 92%, at least 93%, at least 94%, at least 95%, at least 96%, at least 97%, at least 98%, at least 99% or more of the residue at the corresponding site over a certain length of residue is identical. Preferably, the "certain length of residue" can be a residue of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, 85, 90, 95, 100, 105, 110, 115, 120, 125, 130, 135, 140, 145, 150, 155, 160, 165, 160, 165, 170, 175, 180, 185, 190, 195, 200, 205, 210, 215, 220, 225, 230, 235, 240, 245, 250, 255, 260, 265, 270, 275, 280, 285, 290, 295, 300 or more.

In the present invention, the term "corresponding" is often used to determine the position/identity of the amino acid residues of a given polypeptide. As is conventional, residues in a polypeptide are often designated using a canonical numbering system based on reference-related polypeptides. Thus, for example, a "corresponding" amino acid in the residue at the 190th position doesn't always have to be at the 190th position in a particular amino acid chain, and one of ordinary skill in the art will readily understand how to identify the "corresponding" amino acid.

The "functional equivalent" can be a polypeptide that is produced as a result of addition, substitution or deletion of some amino acid sequence of the polypeptide of the present invention. The substitution of the amino acid is preferably a conservative substitution. Examples of conservative substitutions of amino acids present in nature are as follows: aliphatic amino acids (Gly, Ala, Pro), hydrophobic amino acids (Ile, Leu, Val), aromatic amino acids (Phe, Tyr, Trp), acidic amino acids (Asp, Glu), basic amino acids (His, Lys, Arg, Gln, Asn) and sulfur containing amino acids (Cys, Met). Also included in the functional equivalent is variant in which a portion of the amino acid is deleted in the amino acid sequence of the polypeptide of the present invention. The deletion or substitution of the amino acid is preferably located in a region that is not directly related to the physiological activity of the polypeptide of the present invention. In the present invention, the region directly related to the physiological activity is a KGAE region (residues 9 to 12 of SEQ ID NO: 1 or residues 14 to 17 of SEQ ID NO: 5), and the deletion or substitution can be located at a region other than the above-mentioned region. In addition, the deletion of amino acid is preferably located in the region not directly involved in the physiological activity of the polypeptide of the present invention. Also included are variants in which some amino acids are added at both ends or in the sequence of the amino acid of the polypeptide of the present invention. Also included in the functional equivalent of the present invention is protein or polypeptide derivatives in which some of the chemical structures of the proteins are modified while maintaining the basic skeleton and physiological activity of the protein according to the present invention. This includes, for example, structural modifications to alter the stability, shelf stability, volatility or solubility of the protein of the present invention.

In the present invention, sequence homology and identity is defined as the percentage of amino acid residues of the candidate sequence relative to the amino acid sequence of the polypeptide of the present invention after aligning the candidate sequence with the amino acid sequence of the polypeptide of the present invention and introducing a gap. If necessary, conservative substitutions as part of sequence homology are not considered to obtain maximum percent sequence homology. Also, the N-terminal, C-terminal or internal stretch, deletion or insertion of an amino acid sequence of a polypeptide of the invention is not interpreted as a sequence that affects sequence homology or identity. In addition, the sequence homology can be determined by standard methods used to compare similar region of amino acid sequences of two proteins or polypeptides. BLAST or such a computer program aligns two proteins or polypeptides so that each amino acid is optimally matched (along the full length sequence of one or two sequences or along the predicted region of one or two sequences). The program provides default opening penalty and default gap penalty, and provides scoring matrix such as a PAM250 (Standard Scoring Matrix; Dayhoff et al., In Atlas of Protein Sequence & lt; RTI ID=0.0 & gt; Structure, vol 5, supp 3, 1978). For example, percentage homogeneity can be calculated as follows: After multiplying the total number of identical matches by 100 and dividing by the sum of the length of a longer sequence in a matched span and the number of gaps that is introduced into the longer sequence to align the two sequences.

The polypeptides of the present invention can be constructed by genetic engineering methods. First, a polynucleotide sequence encoding the polypeptide of the present invention is constructed according to a conventional method. The polynucleotide sequence can be constructed, for example, by PCR amplification of a polynucleotide encoding the human AIMP1 gene as a template using an appropriate primer. Alternatively, DNA sequences may be synthesized by standard methods known in the art, for example, using an automated DNA synthesizer (commercially available from Biosearch or Applied Biosystems Inc). The constructed polynucleotide is then inserted into a vector comprising one or more expression control sequence (e.g., promoters, enhancers, etc.) which is operatively linked with the polynucleotide so that controls the expression of base sequence of the polynucleotide, followed by transform host cells with the recombinant expression vector. The resulting transgenic cells are cultured under a medium and conditions suitable for the expression of the DNA sequence, and collect substantially pure protein encoded by the DNA sequence from the culture. The collection means separating (isolating) and/or purifying the objective peptide using methods known in the art (e.g. chromatography).

The term "substantially pure polypeptide or protein" means substantially free of any other protein derived from the host cells. Genetic engineering methods for protein synthesis of the present invention can be found in the following references: Maniatis et al., Molecular Cloning; A laboratory Manual, Cold Spring Harbor laboratory, 1982; Sambrook et al., supra; Gene Expression Technology, Method in Enzymology, Genetics and Molecular Biology, Method in Enzymology, Guthrie & Fink (eds.), Academic Press, San Diego, Calif., 1991; and Hitzeman et al., J. Biol. Chem., 255:12073-12080, 1990.

The polypeptides of the present invention can also be chemically synthesized by techniques known in the art (Creighton, Proteins: Structures and Molecular Principles, WH Freeman and Co., NY (1983)). That is, the polypeptides of the present invention can be prepared using conventional stepwise liquid or solid phase synthesis, fractional condensation, F-MOC or T-BOC chemistry (Chemical Approaches to the Synthesis of Peptides and Proteins, Williams et al., Eds., CRC Press, Boca Raton Fla., (1997); A Practical Approach, Atherton & Sheppard, Eds., IRL Press, Oxford, England, (1989)). A preferred method of preparation is solid phase synthesis. The polypeptide of the present invention can be synthesized by a condensation reaction between protected amino acids in a conventional solid-phase method, sequentially proceeding according to the amino acid sequence identified starting from the C-terminal. After the condensation reaction, the protecting group and the carrier to which the C-terminal amino acid is linked can be removed by a known method such as acid decomposition or aminolysis. The above-mentioned peptide synthesis methods are described in detail in the relevant book (Gross and Meienhofer's, The Peptides, vol 2, Academic Press, 1980).

The protein produced by the genetic engineering method or the chemically synthesized protein can be separated and purified by various methods known in the art such as extraction, recrystallization, various chromatography (gel filtration, ion exchange, precipitation, adsorption, reverse phase), electrophoresis, counter current distribution method, etc.

In addition, the present invention provides a polynucleotide encoding the polypeptide of the present invention, that is a polypeptide consisting of 4 to 17 consecutive amino acids from the amino acid sequence of SEQ ID NO: 1, wherein the polypeptide comprises the 9th to 12th amino acid residue (KGAE) of amino acid sequence of SEQ ID NO: 1. The polynucleotide is not particularly limited in its basic constitution as long as it encodes the above-mentioned polypeptide of the present invention. Preferably, the polynucleotide encoding the polypeptide of the invention consists of nucleotide sequence of SEQ ID NO: 7 (encoding S1200 polypeptide of SEQ ID NO: 2) or SEQ ID NO: 8 (encoding S1300 polypeptide of SEQ ID NO: 3).

In the present invention, "polynucleotide", "nucleic acid" refers to a deoxyribonucleotide (DNA) or a ribonucleotide (RNA) in the form of a single-stranded or double-stranded nucleic acid. Unless otherwise limited, it also includes known analogs of natural nucleotides that hybridize to nucleic acids in a manner similar to naturally occurring nucleotides.

Collagen is a fibrous protein that is produced in fibroblasts of the dermis and occupies 70% of the dermis, and is responsible for the flexibility and elasticity of the skin. Therefore, when the synthesis of collagen is reduced, the skin ages and the elasticity and flexibility of the skin are rapidly reduced, resulting in the skin becoming slender or wrinkled. On the other hand, when collagen metabolism is activated by promoting collagen synthesis in the skin, the components of the dermis matrix are increased, thereby improving wrinkles, improving elasticity, and strengthening the skin.

As can be seen from the following examples and figures, the polypeptide fragment of the AIMP1 protein of the present invention has activity of stimulating collagen synthesis and fibroblast proliferation (see Examples 1 and 2, FIGS. 1 to 2). Therefore, the AIMP1 polypeptide fragment of the present invention promotes the synthesis of collagen and/or proliferation of fibroblasts, so that it can be used for preventing skin aging, anti-wrinkle, and improving skin flexibility and elasticity.

In the present invention, the term "skin-aging" refers to an intrinsic aging that is a natural aging phenomenon in which the structure and physiological functions of the skin continuously deteriorate with aging, and an extrinsic aging that is caused by various kind of external factors such as ultraviolet rays, side effects of drugs, stress, environmental factors, scar, and the like. Thus, in the present specification, the term "preventing skin-aging" has a broad meaning including inhibiting, decreasing, preventing or improving the state of skin-aging induced by various causes including intrinsic aging and external aging.

The polypeptide fragment of AIMP1 protein of the present invention can be used as an active ingredient of pharmaceutical, dermatological or cosmetic composition for the use described above.

The composition can be prepared into any formulation conventionally produced in the art. Preferably a formulation for skin application. For example, it can be prepared as a solution, suspension, emulsion, paste, gel, cream, lotion, powder, soap, surfactant-containing cleansing, oil, powder foundation, emulsion foundation, wax foundation and spray, but is not limited to. More preferably, it can be prepared in the form of a soft lotion, a nutritional lotion, a nutritional cream, a massage cream, an essence, an eye cream, a cleansing cream, a cleansing foam, a cleansing water, a pack, a spray or a powder.

In addition, the composition of the present invention can be formulated as injectable formulations for mesotherapy. The injectable formulations can be prepared according to techniques known in the art using suitable dispersing or wetting agents and suspending agents. For example, the polypeptide of the present invention can be formulated for injection by dissolving it in saline or buffer.

The composition of the present invention can also be formulated for oral administration. For oral administration, the polypeptide according to the present invention can be formulated in the form of ingestible tablets, buccal tablets, troches, capsules, elixirs, suspensions, syrups and wafers by mixing with excipients. These formulations can contain diluents (e.g., lactose, dextrose, sucrose, mannitol, sorbitol, cellulose and/or glycine) and lubricants (e.g., silica, talc, stearic acid and magnesium or calcium salts thereof and/or polyethylene glycol). The tablets can contain binders such as magnesium aluminum silicate, starch paste, gelatin, tragacanth, methylcellulose, sodium carboxymethylcellulose and/or polyvinylpyrrolidine, optionally mixed with a disintegrating agent such as sodium salt, starch, agar, an absorbent, a coloring agent, a flavoring agent and/or a sweetening agent. The formulations can be prepared by conventional mixing, granulating or coating methods.

The present invention provides a cosmetic composition for anti-wrinkle, improving skin flexibility and elasticity, the composition comprising as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide. Preferably, the polypeptide can be a polypeptide of SEQ ID NO: 2 or 3.

The present invention also provides a cosmetic composition for anti-wrinkle, improving skin flexibility and elasticity, the composition consisting of as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide. Preferably, the polypeptide can be a polypeptide of SEQ ID NO: 2 or 3.

The present invention provides a cosmetic composition for anti-wrinkle, improving skin flexibility and elasticity, the composition consisting essentially of as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide. Preferably, the polypeptide can be a polypeptide of SEQ ID NO: 2 or 3.

In addition, the present invention provides a cosmetic composition for preventing skin-aging, the composition comprising as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide. Preferably, the polypeptide can be a polypeptide of SEQ ID NO: 2 or 3.

The present invention also provides a cosmetic composition for preventing skin-aging, the composition consisting of as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide. Preferably, the polypeptide can be a polypeptide of SEQ ID NO: 2 or 3.

The present invention provides a cosmetic composition for preventing skin-aging, the composition consisting essentially of as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide. Preferably, the polypeptide can be a polypeptide of SEQ ID NO: 2 or 3.

In addition, the composition of the present invention can further contain known materials having effect on promoting collagen synthesis, promoting fibroblast proliferation, inhibiting/improving skin-aging, moisturizing skin, improving skin elasticity/flexibility, anti-wrinkle, strengthening the function of skin. Such materials include, but are not limited to, retinoic acid, trans-forming growth factor (TGF), betulinic acid, cinnamic acids, hydrostilbene, vitamin A, Vitamin E, vitamin C, red grape extract powder and the like. It may further contain other pharmaceutical, dermatological and/or cosmetically acceptable media or substrates such as substances promoting the absorption of proteins into the skin, preservatives, hydrating agents, emulsifying accelerators, buffers and the like.

The content of the polypeptide of the present invention contained in the cosmetic composition of the present invention can be in the range of 0.0001 to 50% by weight, preferably 0.01 to 10% by weight based on the total weight of the cosmetic composition.

In addition, the present invention provides a food composition for anti-wrinkle, improving skin flexibility and elasticity, the composition comprising as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide. Preferably, the polypeptide can be a polypeptide of SEQ ID NO: 2 or 3.

The present invention also provides a food composition for anti-wrinkle, improving skin flexibility and elasticity, the composition consisting of as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide. Preferably, the polypeptide can be a polypeptide of SEQ ID NO: 2 or 3.

The present invention provides a food composition for anti-wrinkle, improving skin flexibility and elasticity, the composition consisting essentially of as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide. Preferably, the polypeptide can be a polypeptide of SEQ ID NO: 2 or 3.

In addition, the present invention provides a food composition for preventing skin-aging, the composition comprising as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide. Preferably, the polypeptide can be a polypeptide of SEQ ID NO: 2 or 3.

The present invention also provides a food composition for preventing skin-aging, the composition consisting of as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide. Preferably, the polypeptide can be a polypeptide of SEQ ID NO: 2 or 3.

The present invention provides a food composition for preventing skin-aging, the composition consisting essentially of as an active ingredient a polypeptide consisting of 4 to 17 consecutive amino acids from the amino acid sequence of SEQ ID NO: 1, wherein the polypeptide comprises the amino acids KGAE (residues 9 to 12 of SEQ ID NO: 1), or a polypeptide consisting of an amino acid sequence having 70% or more sequence homology with the polypeptide. Preferably, the polypeptide can be a polypeptide of SEQ ID NO: 2 or 3.

The food composition of the present invention includes all forms such as functional food, nutritional supplement, health food and food additives. These types can be prepared in various forms according to conventional methods known in the art.

For example, as the health food, the food composition itself of the present invention can be prepared in the form of tea, juice, and drink, and can be ingested as granulated, encapsulated, and powdered form. In addition, the food composition of the present invention can be prepared in the form of a composition by mixing with a known substance or active ingredient known to have the effect on anti-wrinkle, preventing skin-aging, and improving skin flexibility and elasticity.

In addition, the functional foods also include beverages (including alcoholic beverages), fruits and their processed foods (e.g., canned fruits, bottled, jam, maalmalade, etc.), fish, meats and processed foods (e.g., ham, etc.), breads and noodles (e.g., udon, buckwheat noodles, ramen noodles, spaghetti, macaroni, etc.), juice, various drinks, cookies, yeot, dairy products (e.g., butter, cheeses, etc.), edible plant oils, margarine, vegetable protein, retort food, frozen food, various kinds of seasoning (e.g., soybean paste, soy sauce, sauce, etc.).

The preferred content of the food composition of the polypeptide of the present invention is not particularly limited, but is preferably 0.01 to 50% by weight in the finally prepared food. In order to use the food composition of the present invention in the form of a food additive, it can be prepared in the form of powder or concentrate.

The present invention provides use of the polypeptide for preparing an agent for anti-wrinkle, improving skin flexibility and elasticity.

The present invention provides a method for anti-wrinkle, improving skin flexibility and elasticity, the method comprising administering to a subject in need thereof an effective amount of the polypeptide.

The present invention provides use of the polypeptide for preparing an agent for preventing skin-aging.

The present invention provides a method for preventing skin-aging, the method comprising administering to a subject in need thereof an effective amount of the polypeptide.

The 'effective amount' of the present invention refers to an amount that, when administered to an individual, represents effect on improving, treating, preventing, detecting or diagnosing skin-aging. And the "individual" includes an animal, preferably a mammal, in particular may be an animal comprising human, an animal-derived cell, tissue, organs, and the like. The subject can be a patient requiring the effect.

The term "treatment" of the present invention broadly refers to the amelioration of symptoms related to skin wrinkles, skin elasticity, skin flexibility or skin-aging, and it can include treating, substantially preventing, or improving the state of such diseases. And it can also include alleviating, treating or preventing a symptom or most symptoms caused by such diseases, but not limited thereto.

The term "comprising" of the present invention is used synonymously with "containing" or "characterized in that" and does not exclude additional component elements or method steps not mentioned in the composition or method. The term "consisting of" refers to exclude additional elements, steps or components not otherwise mentioned. The term "consisting essentially of" is intended to encompass component elements or steps, etc., which, in addition to the described component elements or steps, do not substantially affect their underlying properties.

Advantageous Effects

Accordingly, the present invention provides novel fragments of AIMP1 protein and a composition comprising the same as an active ingredient for preventing skin-aging, anti-wrinkle, and improving skin flexibility and elasticity. The novel polypeptide according to the present invention and the composition comprising the same as an active ingredient can be used for preventing skin-aging, anti-wrinkle, and improving skin flexibility and elasticity.

MODE FOR CARRYING OUT THE INVENTION

Figure 1:
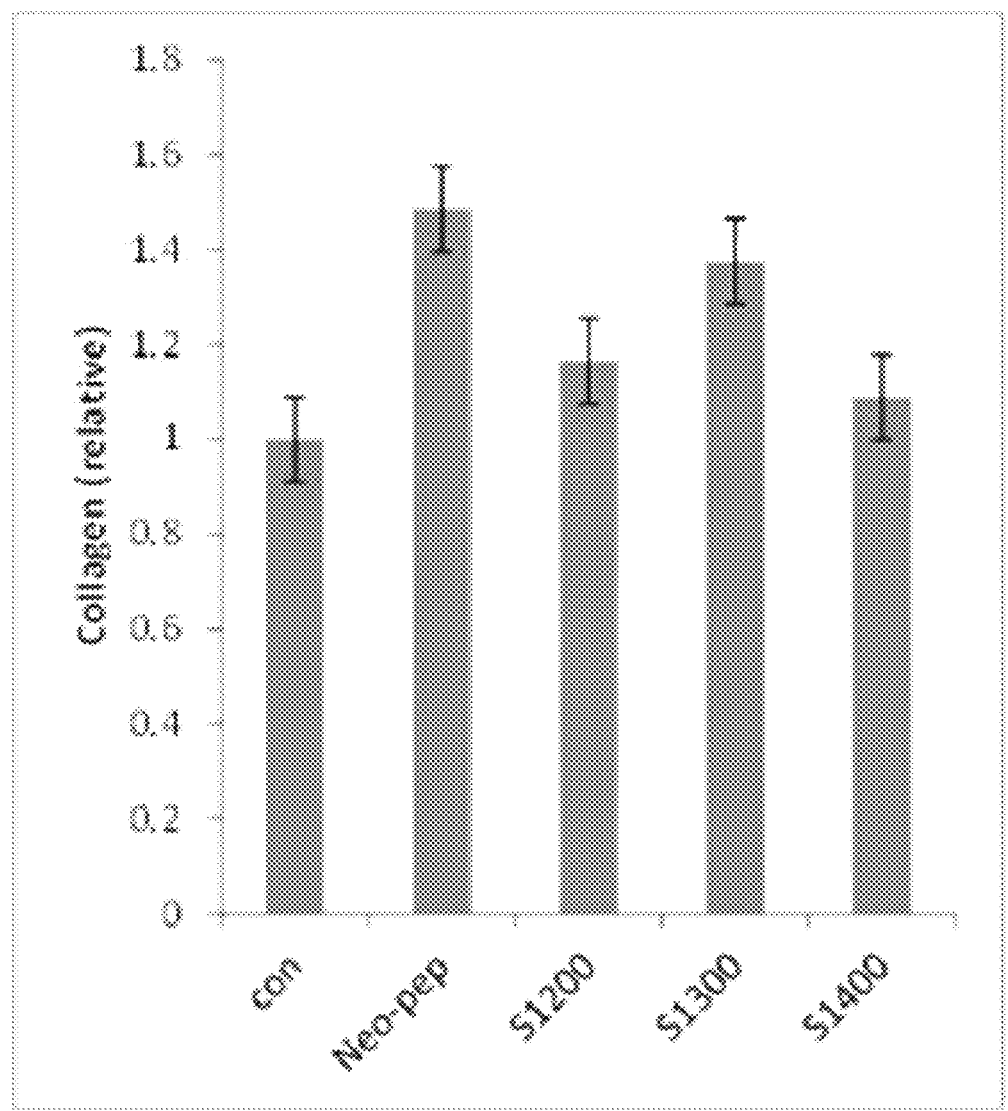
FIG. 1 is a graph showing the results of a Procollagen Type I ELISA Assay in which collagen synthesis induction effect of the Neo-Pep polypeptide (SEQ ID NO: 1, 10 μM) and its peptide fragments (SEQ ID NOs: 2 to 4, 10 μM) was confirmed [Control (Con): 20% Glycerol/PBS (10 μg/ml); Neo-Pep polypeptide (SEQ ID NO: 1), S1200 (SEQ ID NO: 2), S1300 (SEQ ID NO: 3), S1400 (SEQ ID NO: 4)].

Hereinafter, the present invention will be described in detail.

However, the following examples are merely for illustrating the present invention and are not intended to limit the scope of the present invention.

Method

1. Collagen ELISA Assay

Human foreskin fibroblast ($1.5 \times 10^4$ cells/well; Promocell) was cultured in DMEM medium containing 10% serum in a 24-well plate for 12 hours and then cultured in serum-free medium for about 3 hours. Then, Neo-Pep polypeptide (SEQ ID NO: 1,) and its fragments (SEQ ID NOs: 2 to 4, synthesized at GL Biochem) were added to the DMEM medium with the concentration of 10 μM each, and then cultured for 12 hours.

Thereafter, the medium was collected, centrifuged at 1,000 g for 10 minutes, and then secreted collagen was detected in accordance with the manufacturer's instructions using a Procollagen Type I ELISA kit (Takara, Japan).

2. Cell Proliferation and Cytotoxicity Assay (Cell Counting Kit-8 Assay)

To confirm the proliferation and cytotoxicity of the fibroblasts, the CCK-8 assay (Cell Counting Kit-8 assay) of Dojindo Molecular Technologies (Japan) was performed according to the manufacturer's instructions.

First, human foreskin fibroblast (3,000 cells/well; Promocell) and normal epithelium cells (vero; 3,000 cells/well) were cultured in DMEM medium containing 10% serum in 96-well plates for 12 hours, and then cultured in serum-free medium for about 3 hours. Then, Neo-Pep polypeptide (SEQ ID NO: 1) and fragments thereof (SEQ ID NOS: 2 to 4) were added to the DMEM medium with the concentration of 10 μM each, and then cultured for 24 hours.

Then, 10 μl of CCK-8 solution (Dojindo Molecular Technologies, Japan) was added to each well of the medium, and the absorbance was analyzed at 450 nm using a microplate reader according to the manufacturer's instructions.

3. TNF-Alpha ELISA Assay

Raw 264.7 cells (ATCC TIB-71; 3,000 cells/well) were cultured for 12 hours in DMEM medium containing 10% serum in a 96-well plate, and then cultured in serum-free medium for about 3 hours. Then, Neo-Pep polypeptide (SEQ ID NO: 1) and its fragments (SEQ ID NOS: 2 to 4) were added to the DMEM medium with the concentration of 10 μM each, and then cultured for 6 hours.

Then, the medium was collected and centrifuged at 1,000 g for 10 minutes, and secreted TNF-α was detected using a TNF-α ELISA assay (BD Biosciences, USA) according to the manufacturer's instructions.

Example 1: Collagen Synthesis Inducing Effect of the Polypeptides of the Present Invention The present inventor prepared S1200 (SEQ ID NO: 2), S1300 (SEQ ID NO: 3), S1400 (SEQ ID NO: 4), the fragments of the Neo-Pep polypeptide and composed of 15 amino acids, in order to confirmed the effect of the polypeptide of the present invention on preventing skin-aging, anti-wrinkle, and improving skin flexibility and elasticity.

Table 1 below shows the amino acid sequence, PI and Tm of Neo-Pep (SEQ ID NO: 1) and its fragments, S1200 (SEQ ID NO: 2), S1300 (SEQ ID NO: 3), S1400 (SEQ ID NO: 4).

TABLE 1

| Polypeptide (SEQ ID) | Amino acid sequence | PI | Tm |
|---|---|---|---|
| Neo-Pep (SEQ ID NO: 1) | AVLKRLEQKGAEADQIIEYLK 46 QQVSLLKEKAILQATLREEK | 9.33 | >65 |
| S1200 (SEQ ID NO: 2) | RLEQKGAEADQIIEY | 4.04 | <55 |
| S1300 (SEQ ID NO: 3) | KGAEADQIIEYLKQQ | 4.43 | 55~65 |
| S1400 (SEQ ID NO: 4) | IEYLKQQVSLLKEKA | 9.53 | >65 |

For reference, the polypeptide Neo-Pep (SEQ ID NO: 1) of the present invention corresponds to residues 6 to 46 of SEQ ID NO: 5 in the AIMP1 protein (SEQ ID NO: 5).

MANNDAVLKRLEQKGAEADQIIEYLKQQVSLLKEKAILQATLREEKKLRV
ENAKLKKEIEELKQELIQAEIQNGVKQIPFPSGTPLHANSMVSENVIQST
AVTTVSSGTKEQIKGGTGDEKKAKEKIEKKGEKKEKKQQSIAGSADSKPI
DVSRLDLRIGCIITARKHPDADSLYVEEVDVGEIAPRTVVSGLVNHVPLE
QMQNRMVILLCNLKPAKMRGVLSQAMVMCASSPEKIEILAPPNGSVPGDR
ITFDAFPGEPDKELNPKKKIWEQIQPDLHTNDECVATYKGVPFEVKGKGV
CRAQTMSNSGIK

As can be seen from FIG. 1, as a result of the Procollagen type I ELISA assay method described above, the Neo-Pep polypeptide (SEQ ID NO: 1) and the fragments of the Neo-Pep polypeptide consisting of 15 consecutive amino acids and comprising amino acids KGAE (residues 9 to 12 of SEQ ID NO: 1) of the Neo-Pep polypeptide (S1200 (SEQ ID NO: 2), S1300 (SEQ ID NO: 3)) induced collagen synthesis more than control group (Con).

Figure 2:
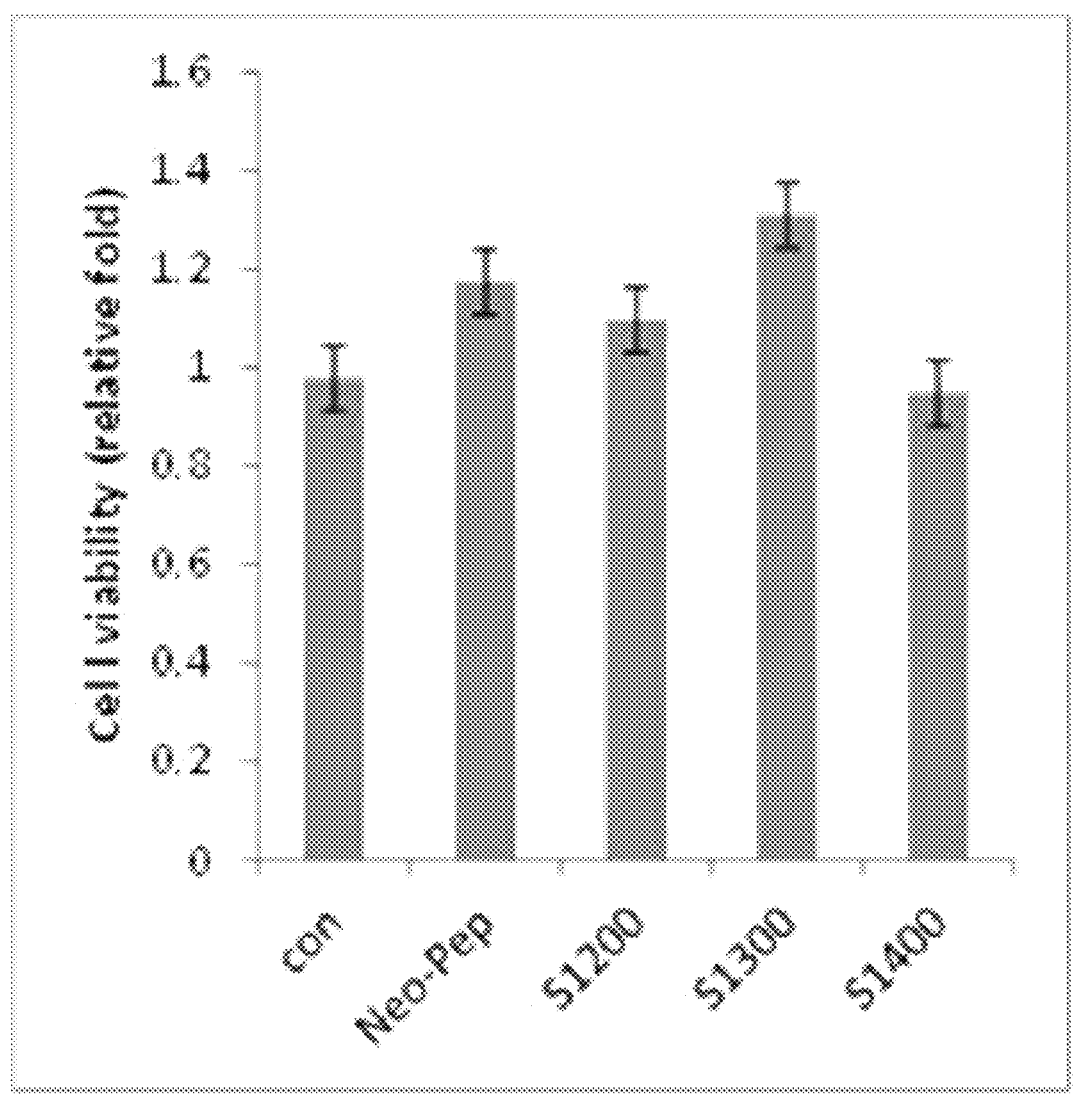
FIG. 2 is a graph showing the results of a Cell Counting Kit-8 Assay in which human fibroblast proliferation induction effect of the Neo-Pep polypeptide (SEQ ID NO: 1, 10 μM) and its peptide fragments (SEQ ID NOs: 2 to 4, 10 μM) was confirmed [Control (Con): 20% Glycerol/PBS (10 μg/ml); Neo-Pep polypeptide (SEQ ID NO: 1), S1200 (SEQ ID NO: 2), S1300 (SEQ ID NO: 3), S1400 (SEQ ID NO: 4)].

And, the fragment (S1400 (SEQ ID NO: 4) of the Neo-Pep polypeptide (SEQ ID NO: 1) consisting of 15 consecutive amino acids without amino acids KGAE (residues 9 to 12 of SEQ ID NO: 1) of the Neo-Pep polypeptide showed slightly better effect on inducing collagen synthesis than control group, but as can be seen in FIG. 2, its effect on inducing proliferation of fibroblast was lower than control group.

Example 2: Fibroblast Proliferation Inducing Effect of the Polypeptides of the Present Invention As can be seen from FIG. 2, as a result of the CCK-8 Assay method described above, the Neo-Pep polypeptide (SEQ ID NO: 1) and the fragments of the Neo-Pep polypeptide consisting of 15 consecutive amino acids and comprising amino acids KGAE (residues 9 to 12 of SEQ ID NO: 1) of the Neo-Pep polypeptide (S1200 (SEQ ID NO: 2), S1300 (SEQ ID NO: 3)) induced proliferation of fibloblast more than control group (Con).

On the other hand, the fragment (S1400 (SEQ ID NO: 4) of the Neo-Pep (SEQ ID NO: 1) consisting of 15 consecutive amino acids without amino acids KGAE (residues 9 to 12 of SEQ ID NO: 1) of the Neo-Pep polypeptide showed lower effect on inducing proliferation of fibloblast than control group.

Through the above results of Example 1 and 2, it was confirmed that polypeptide fragments comprising amino acids KGAE (residues 9 to 12 of SEQ ID NO: 1) of the Neo-Pep polypeptide (SEQ ID NO: 1) and consisting of consecutive amino acids such as S1200 (SEQ ID NO: 1) and S1300 (SEQ ID NO: 3) induce synthesis of collagen and proliferation of fibroblast, so that have effect on preventing skin-aging, anti-wrinkle, and improving skin flexibility and elasticity.

Figure 3:
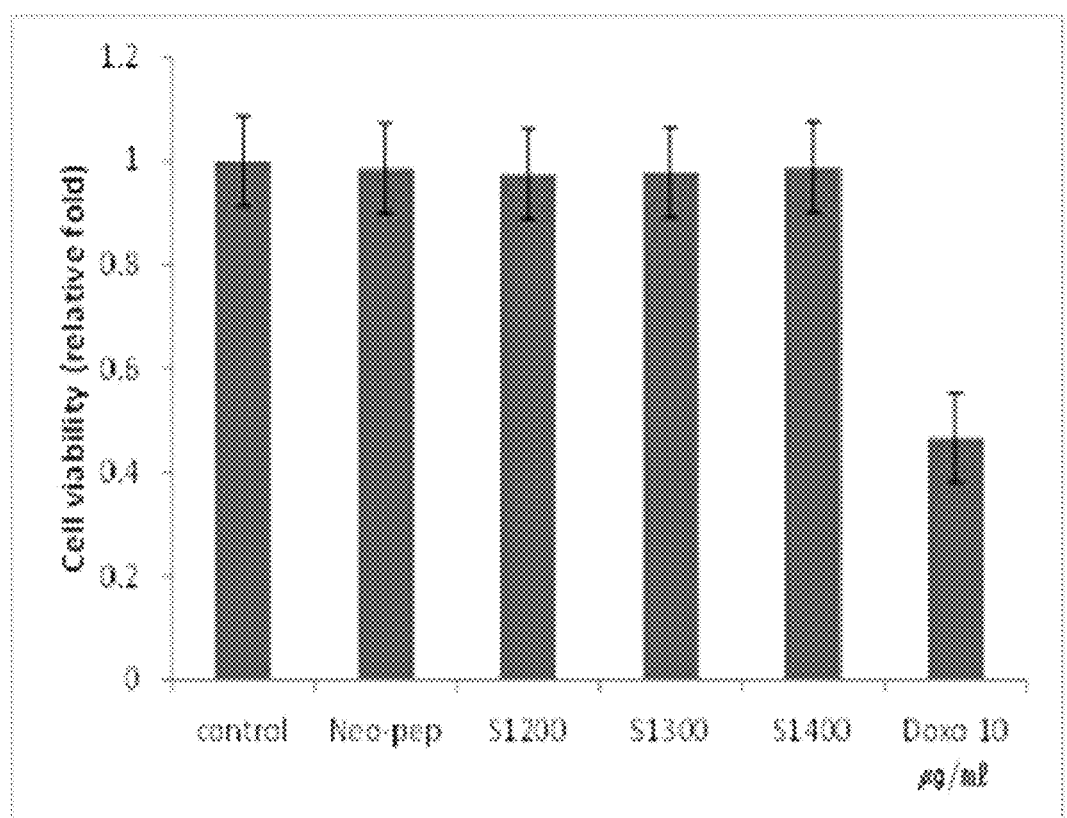
FIG. 3 is a graph showing the results of a cytotoxicity assay (Cell Counting Kit-8 assay) in which cytotoxicity of the Neo-Pep polypeptide (SEQ ID NO: 1, 10 μM) and its peptide fragments (SEQ ID NOs: 2 to 4, 10 μM) on normal epidermis cell (vero) was confirmed [Control (Con): 20% Glycerol/PBS (10 μg/ml); Neo-Pep polypeptide (SEQ ID NO: 1), S1200 (SEQ ID NO: 2), S1300 (SEQ ID NO: 3), S1400 (SEQ ID NO: 4), Doxo (Doxorubicin (10 μg/ml)].

Example 3: Confirming the Presence of Cytotoxicity and Inflammation Induction with the Polypeptides of the Present Invention As can be seen in FIG. 3, as a result of CCK-8 Assay method described above, the epithelium cell viability of the groups treated with Neo-Pep polypeptide (SEQ ID NO: 1), S1200 (SEQ ID NO: 2) or S1300 (SEQ ID NO: 3) was similar to that of control group showing its safety, but the epithelium cell viability of the group treated with the fragment (S1400 (SEQ ID NO: 4)) without amino acids KGAE (residues 9 to 12 of SEQ ID NO: 1) of Neo-Pep polypeptide (SEQ ID NO: 1) was slightly lower. For reference, Doxorubicin (10 µg/ml), a potent cytotoxic agent, was used in order to compare the cytotoxicity.

Figure 4:
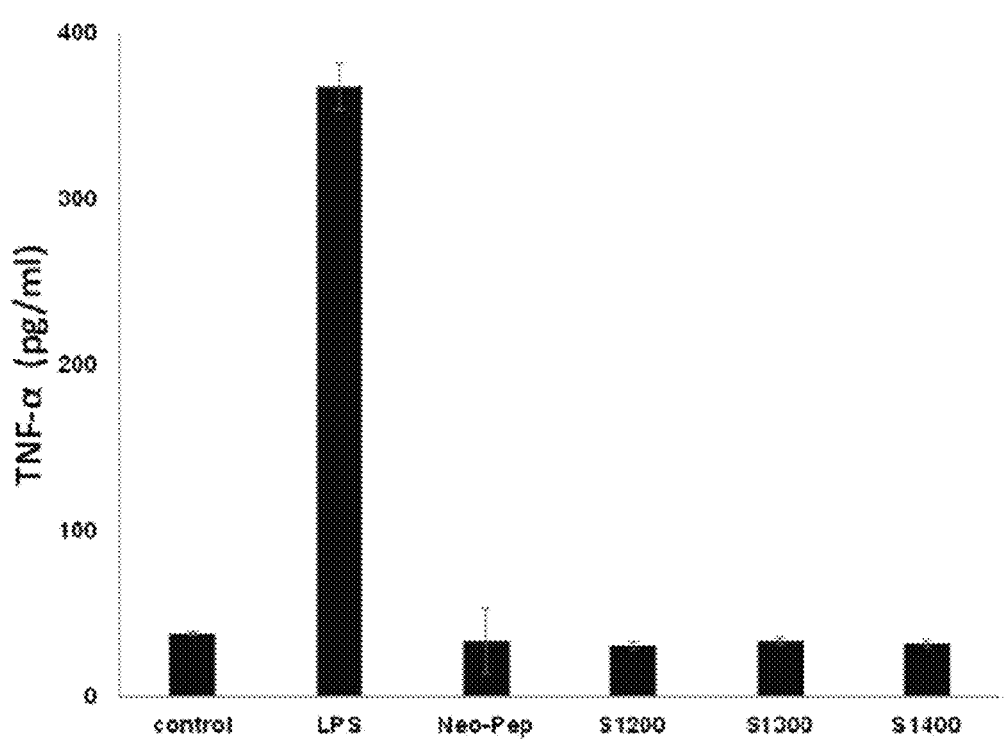
FIG. 4 is a graph showing the results of a TNF-alpha ELISA assay in which the amount of TNF-alpha secretion on Raw 264.7 cells treated with the Neo-Pep polypeptide (SEQ ID NO: 1, 10 μM) and its peptide fragments (SEQ ID NOs: 2 to 4, 10 μM) was confirmed [Control (Con): 20% Glycerol/PBS (10 μg/ml); Neo-Pep polypeptide (SEQ ID NO: 1), S1200 (SEQ ID NO: 2), S1300 (SEQ ID NO: 3), S1400 (SEQ ID NO: 4), LPS (lipopolysaccharide, 10 ng/ml)].

In addition, as can be seen in FIG. 4, as a result of TNF-alpha ELISA assay described above, the secreted TNF-alpha level of the group treated with Neo-Pep polypeptide (SEQ ID NO: 1), S1200 (SEQ ID NO: 2), S1300 (SEQ ID NO: 3) or S1400 (SEQ ID NO: 4) was very low and similar to that of control group showing that almost no immune reaction such as inflammation was induced. Therefore, it was suggested that they are safe to use in body. For reference, LPS (lipopolysaccharide, 10 ng/ml), a potent endotoxin inducing immune reaction, was used in order to compare the extent of induction of immune reaction such as inflammation.

The invention claimed is:

1. A polypeptide consisting of 4 to 17 consecutive amino acids from the amino acid sequence of SEQ ID NO: 1, wherein the 4 to 17 consecutive amino acids include residues 9 to 12 of SEQ ID NO: 1, and improves skin flexibility and elasticity, inhibits or decreases skin aging, and/or has anti-wrinkle activity.

2. The polypeptide of claim 1, wherein the polypeptide consists of 10 to 15 consecutive amino acids from the amino acid sequence of SEQ ID NO: 1 and wherein the 10 to 15 consecutive amino acids include residues 9 to 12 of SEQ ID NO: 1.

3. The polypeptide of claim 1, wherein the polypeptide consists of the amino acid sequence of SEQ ID NO: 2 or SEQ ID NO: 3.

4. A composition for improving skin flexibility and elasticity, inhibiting or decreasing skin aging, and/or having anti-wrinkle activity, comprising as an active ingredient a polypeptide consisting of 4 to 17 consecutive amino acids from the amino acid sequence of SEQ ID NO: 1, wherein 4 to 17 consecutive amino acids includes residues 9 to 12 of SEQ ID NO: 1 of SEQ ID NO: 1.

5. The composition of claim 4, wherein the polypeptide consists of the amino acid sequence of SEQ ID NO: 2 or SEQ ID NO: 3.

6. The composition of claim 4, wherein the composition is for a cosmetic composition, or a food composition.

7. The composition of claim 6, wherein the composition is a cosmetic composition and the polypeptide is present in a range of 0.0001 to 50% by weight of the cosmetic composition.

8. The composition of claim 7, wherein the polypeptide is present in a range of 0.01 to 10% by weight of the cosmetic composition.

9. The composition of claim 6, wherein the composition is a food composition and the polypeptide is present in a range of 0.01 to 50% by weight of the food composition.

10. A method for anti-wrinkle, improving skin flexibility and elasticity, the method comprising administering to a subject in need thereof an effective amount of the polypeptide of claim 1.

11. A method for inhibiting or decreasing skin-aging, the method comprising administering to a subject in need thereof an effective amount of the polypeptide of claim 1.

* * * * *

SEQUENCE LISTING

```
<160> NUMBER OF SEQ ID NOS: 13

<210> SEQ ID NO 1
<211> LENGTH: 41
<212> TYPE: PRT
<213> ORGANISM: Artificial Sequence
<220> FEATURE:
<223> OTHER INFORMATION: Homo sapiens Neo-Pep polypeptide; AIMP1-(6-46)

<400> SEQUENCE: 1

Ala Val Leu Lys Arg Leu Glu Gln Lys Gly Ala Glu Ala Asp Gln Ile
1               5                   10                  15

Ile Glu Tyr Leu Lys Gln Gln Val Ser Leu Leu Lys Glu Lys Ala Ile
            20                  25                  30

Leu Gln Ala Thr Leu Arg Glu Glu Lys
        35                  40

<210> SEQ ID NO 2
<211> LENGTH: 15
<212> TYPE: PRT
<213> ORGANISM: Artificial Sequence
<220> FEATURE:
<223> OTHER INFORMATION: Homo sapiens S1200 polypeptide; Neo-Pep-(5-19)

<400> SEQUENCE: 2

Arg Leu Glu Gln Lys Gly Ala Glu Ala Asp Gln Ile Ile Glu Tyr
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Homo sapiens S1300 polypeptide; Neo-Pep-(9-23)

<400> SEQUENCE: 3

Lys Gly Ala Glu Ala Asp Gln Ile Ile Glu Tyr Leu Lys Gln Gln
1               5                   10                  15

<210> SEQ ID NO 4
<211> LENGTH: 15
<212> TYPE: PRT
<213> ORGANISM: Artificial Sequence
<220> FEATURE:
```

```
<223> OTHER INFORMATION: Homo sapiens S1400 polypeptide; Neo-Pep-(17-31)

<400> SEQUENCE: 4

Ile Glu Tyr Leu Lys Gln Gln Val Ser Leu Leu Lys Glu Lys Ala
1               5                   10                  15

<210> SEQ ID NO 5
<211> LENGTH: 312
<212> TYPE: PRT
<213> ORGANISM: Artificial Sequence
<220> FEATURE:
<223> OTHER INFORMATION: homo sapiens AIMP1 protein

<400> SEQUENCE: 5

Met Ala Asn Asn Asp Ala Val Leu Lys Arg Leu Glu Gln Lys Gly Ala
1               5                   10                  15

Glu Ala Asp Gln Ile Ile Glu Tyr Leu Lys Gln Gln Val Ser Leu Leu
                20                  25                  30

Lys Glu Lys Ala Ile Leu Gln Ala Thr Leu Arg Glu Glu Lys Lys Leu
            35                  40                  45

Arg Val Glu Asn Ala Lys Leu Lys Lys Glu Ile Glu Glu Leu Lys Gln
    50                  55                  60

Glu Leu Ile Gln Ala Glu Ile Gln Asn Gly Val Lys Gln Ile Pro Phe
65                  70                  75                  80

Pro Ser Gly Thr Pro Leu His Ala Asn Ser Met Val Ser Glu Asn Val
                85                  90                  95

Ile Gln Ser Thr Ala Val Thr Thr Val Ser Ser Gly Thr Lys Glu Gln
            100                 105                 110

Ile Lys Gly Gly Thr Gly Asp Glu Lys Lys Ala Lys Glu Lys Ile Glu
        115                 120                 125

Lys Lys Gly Glu Lys Lys Glu Lys Lys Gln Gln Ser Ile Ala Gly Ser
    130                 135                 140

Ala Asp Ser Lys Pro Ile Asp Val Ser Arg Leu Asp Leu Arg Ile Gly
145                 150                 155                 160

Cys Ile Ile Thr Ala Arg Lys His Pro Asp Ala Asp Ser Leu Tyr Val
                165                 170                 175

Glu Glu Val Asp Val Gly Glu Ile Ala Pro Arg Thr Val Val Ser Gly
            180                 185                 190

Leu Val Asn His Val Pro Leu Glu Gln Met Gln Asn Arg Met Val Ile
        195                 200                 205

Leu Leu Cys Asn Leu Lys Pro Ala Lys Met Arg Gly Val Leu Ser Gln
    210                 215                 220

Ala Met Val Met Cys Ala Ser Ser Pro Glu Lys Ile Glu Ile Leu Ala
225                 230                 235                 240

Pro Pro Asn Gly Ser Val Pro Gly Asp Arg Ile Thr Phe Asp Ala Phe
                245                 250                 255

Pro Gly Glu Pro Asp Lys Glu Leu Asn Pro Lys Lys Lys Ile Trp Glu
            260                 265                 270

Gln Ile Gln Pro Asp Leu His Thr Asn Asp Glu Cys Val Ala Thr Tyr
        275                 280                 285

Lys Gly Val Pro Phe Glu Val Lys Gly Lys Gly Val Cys Arg Ala Gln
    290                 295                 300

Thr Met Ser Asn Ser Gly Ile Lys
305                 310

<210> SEQ ID NO 6
```

```
<211> LENGTH: 123
<212> TYPE: DNA
<213> ORGANISM: Artificial Sequence
<220> FEATURE:
<223> OTHER INFORMATION: Homo sapiens Neo-Pep AIMP1- (6-46)
      polynuceotide

<400> SEQUENCE: 6
gctgttctga agagactgga gcagaagggt gcagaggcag atcaaatcat tgaatatctt      60
aagcagcaag tttctctact taaggagaaa gcaattttgc aggcaacttt gagggaagag     120
aag                                                                   123

<210> SEQ ID NO 7
<211> LENGTH: 45
<212> TYPE: DNA
<213> ORGANISM: Artificial Sequence
<220> FEATURE:
<223> OTHER INFORMATION: Homo sapiens S1200 Neo-Pep-(5-19)
      polynucleotide

<400> SEQUENCE: 7
agactggagc agaagggtgc agaggcagat caaatcattg aatat                      45

<210> SEQ ID NO 8
<211> LENGTH: 45
<212> TYPE: DNA
<213> ORGANISM: Artificial Sequence
<220> FEATURE:
<223> OTHER INFORMATION: Homo sapiens S1300 Neo-Pep-(9-23)
      polynucleotide

<400> SEQUENCE: 8
aagggtgcag aggcagatca aatcattgaa tatcttaagc agcaa                      45

<210> SEQ ID NO 9
<211> LENGTH: 45
<212> TYPE: DNA
<213> ORGANISM: Artificial Sequence
<220> FEATURE:
<223> OTHER INFORMATION: Homo sapiens S1400 Neo-Pep-(17-31)
      polynucloetide

<400> SEQUENCE: 9
attgaatatc ttaagcagca agtttctcta cttaaggaga aagca                      45

<210> SEQ ID NO 10
<211> LENGTH: 936
<212> TYPE: DNA
<213> ORGANISM: Artificial Sequence
<220> FEATURE:
<223> OTHER INFORMATION: Homo sapiens AIMP1 polynucleotide

<400> SEQUENCE: 10
atggcaaata tgatgctgt tctgaagaga ctggagcaga agggtgcaga ggcagatcaa       60
atcattgaat atcttaagca gcaagtttct ctacttaagg agaaagcaat tttgcaggca     120
actttgaggg aagagaagaa acttcgagtt gaaaatgcta aactgaagaa agaaattgaa     180
gaactgaaac aagagctaat tcaggcagaa attcaaaatg gagtgaagca ataccatttt     240
ccatctggta ctccactgca cgctaattct atggtttctg aaaatgtgat acagtctaca     300
gcagtaacaa ccgtatcttc tggtaccaaa gaacagataa aggaggaac aggagacgaa      360 aagaaagcga aagagaaaat tgaaagaaa ggagagaaga aggagaaaaa acagcaatca     420
atagctggaa gtgccgactc taagccaata gatgtttccc gtctggatct tcgaattggt     480
```

-continued

```
tgcatcataa ctgctagaaa acaccctgat gcagattctt tgtatgtgga agaagtagat      540
gtcggagaaa tagccccaag gacagttgtc agtggcctgg tgaatcatgt tcctcttgaa      600
cagatgcaaa atcggatggt gattttactt tgtaacctga aacctgcaaa gatgagggga      660
gtattatctc aagcaatggt catgtgtgct agttcaccag agaaaattga atcttggct       720 cctccaaatg ggtctgttcc tggagacaga attactttg atgctttccc aggagagcct       780
gacaaggagc tgaatcctaa gaagaagatt tgggagcaga tccagcctga tcttcacact      840
aatgatgagt gtgtggctac atacaaagga gttccctttg aggtgaaagg aagggagta       900 tgtagggctc aaaccatgag caacagtgga atcaaa                                936
```

<210> SEQ ID NO 11
<211> LENGTH: 312
<212> TYPE: PRT
<213> ORGANISM: Artificial Sequence
<220> FEATURE:
<223> OTHER INFORMATION: homo sapiens AIMP1 protein

<400> SEQUENCE: 11

```
Met Ala Asn Asn Asp Ala Val Leu Lys Arg Leu Glu Gln Lys Gly Ala
1               5                   10                  15

Glu Ala Asp Gln Ile Ile Glu Tyr Leu Lys Gln Gln Val Ser Leu Leu
            20                  25                  30

Lys Glu Lys Ala Ile Leu Gln Ala Thr Leu Arg Glu Glu Lys Lys Leu
        35                  40                  45

Arg Val Glu Asn Ala Lys Leu Lys Lys Glu Ile Glu Glu Leu Lys Gln
    50                  55                  60

Glu Leu Ile Gln Ala Glu Ile Gln Asn Gly Val Lys Gln Ile Ala Phe
65                  70                  75                  80

Pro Ser Gly Thr Pro Leu His Ala Asn Ser Met Val Ser Glu Asn Val
                85                  90                  95

Ile Gln Ser Thr Ala Val Thr Thr Val Ser Ser Gly Thr Lys Glu Gln
            100                 105                 110

Ile Lys Gly Gly Thr Gly Asp Glu Lys Lys Ala Lys Glu Lys Ile Glu
        115                 120                 125

Lys Lys Gly Glu Lys Lys Glu Lys Lys Gln Gln Ser Ile Ala Gly Ser
    130                 135                 140

Ala Asp Ser Lys Pro Ile Asp Val Ser Arg Leu Asp Leu Arg Ile Gly
145                 150                 155                 160

Cys Ile Ile Thr Ala Arg Lys His Pro Asp Ala Asp Ser Leu Tyr Val
                165                 170                 175

Glu Glu Val Asp Val Gly Glu Ile Ala Pro Arg Thr Val Val Ser Gly
            180                 185                 190

Leu Val Asn His Val Pro Leu Glu Gln Met Gln Asn Arg Met Val Ile
        195                 200                 205

Leu Leu Cys Asn Leu Lys Pro Ala Lys Met Arg Gly Val Leu Ser Gln
    210                 215                 220

Ala Met Val Met Cys Ala Ser Ser Pro Glu Lys Ile Glu Ile Leu Ala
225                 230                 235                 240

Pro Pro Asn Gly Ser Val Pro Gly Asp Arg Ile Thr Phe Asp Ala Phe
                245                 250                 255

Pro Gly Glu Pro Asp Lys Glu Leu Asn Pro Lys Lys Lys Ile Trp Glu
            260                 265                 270

Gln Ile Gln Pro Asp Leu His Thr Asn Asp Glu Cys Val Ala Thr Tyr
```

```
            275                 280                 285
Lys Gly Val Pro Phe Glu Val Lys Gly Lys Gly Val Cys Arg Ala Gln
    290                 295                 300

Thr Met Ser Asn Ser Gly Ile Lys
305                 310

<210> SEQ ID NO 12
<211> LENGTH: 312
<212> TYPE: PRT
<213> ORGANISM: Artificial Sequence
<220> FEATURE:
<223> OTHER INFORMATION: homo sapiens AIMP1 protein

<400> SEQUENCE: 12

Met Ala Asn Asn Asp Ala Val Leu Lys Arg Leu Glu Gln Lys Gly Ala
1               5                   10                  15

Glu Ala Asp Gln Ile Ile Glu Tyr Leu Lys Gln Gln Val Ser Leu Leu
                20                  25                  30

Lys Glu Lys Ala Ile Leu Gln Ala Thr Leu Arg Glu Glu Lys Lys Leu
        35                  40                  45

Arg Val Glu Asn Ala Lys Leu Lys Lys Glu Ile Glu Glu Leu Lys Gln
    50                  55                  60

Glu Leu Ile Gln Ala Glu Ile Gln Asn Gly Val Lys Gln Ile Ala Phe
65              70                  75                  80

Pro Ser Gly Thr Pro Leu His Ala Asn Ser Met Val Ser Glu Asn Val
                85                  90                  95

Ile Gln Ser Thr Ala Val Thr Ala Val Ser Ser Gly Thr Lys Glu Gln
            100                 105                 110

Ile Lys Gly Gly Thr Gly Asp Glu Lys Lys Ala Lys Glu Lys Ile Glu
        115                 120                 125

Lys Lys Gly Glu Lys Lys Glu Lys Lys Gln Gln Ser Ile Ala Gly Ser
    130                 135                 140

Ala Asp Ser Lys Pro Ile Asp Val Ser Arg Leu Asp Leu Arg Ile Gly
145                 150                 155                 160

Cys Ile Ile Thr Ala Arg Lys His Pro Asp Ala Asp Ser Leu Tyr Val
                165                 170                 175

Glu Glu Val Asp Val Gly Glu Ile Ala Pro Arg Thr Val Val Ser Gly
            180                 185                 190

Leu Val Asn His Val Pro Leu Glu Gln Met Gln Asn Arg Met Val Ile
        195                 200                 205

Leu Leu Cys Asn Leu Lys Pro Ala Lys Met Arg Gly Val Leu Ser Gln
    210                 215                 220

Ala Met Val Met Cys Ala Ser Ser Pro Glu Lys Ile Glu Ile Leu Ala
225                 230                 235                 240

Pro Pro Asn Gly Ser Val Pro Gly Asp Arg Ile Thr Phe Asp Ala Phe
                245                 250                 255

Pro Gly Glu Pro Asp Lys Glu Leu Asn Pro Lys Lys Lys Ile Trp Glu
            260                 265                 270

Gln Ile Gln Pro Asp Leu His Thr Asn Asp Glu Cys Val Ala Thr Tyr
        275                 280                 285

Lys Gly Val Pro Phe Glu Val Lys Gly Lys Gly Val Cys Arg Ala Gln
    290                 295                 300

Thr Met Ser Asn Ser Gly Ile Lys
305                 310
```

```
<210> SEQ ID NO 13
<211> LENGTH: 312
<212> TYPE: PRT
<213> ORGANISM: Artificial Sequence
<220> FEATURE:
<223> OTHER INFORMATION: homo sapiens AIMP1 protein

<400> SEQUENCE: 13

Met Ala Asn Asn Asp Ala Val Leu Lys Arg Leu Glu Gln Lys Gly Ala
1               5                   10                  15

Glu Ala Asp Gln Ile Ile Glu Tyr Leu Lys Gln Gln Val Ser Leu Leu
                20                  25                  30

Lys Glu Lys Ala Ile Leu Gln Ala Thr Leu Arg Glu Glu Lys Lys Leu
            35                  40                  45

Arg Val Glu Asn Ala Lys Leu Lys Lys Glu Ile Glu Glu Leu Lys Gln
    50                  55                  60

Glu Leu Ile Gln Ala Glu Ile Gln Asn Gly Val Lys Gln Ile Ala Phe
65                  70                  75                  80

Pro Ser Gly Thr Pro Leu His Ala Asn Ser Met Val Ser Glu Asn Val
                85                  90                  95

Ile Gln Ser Thr Ala Val Thr Thr Val Ser Ser Gly Thr Lys Glu Gln
                100                 105                 110

Ile Lys Gly Gly Ala Gly Asp Glu Lys Lys Ala Lys Glu Lys Ile Glu
            115                 120                 125

Lys Lys Gly Glu Lys Lys Glu Lys Lys Gln Gln Ser Ile Ala Gly Ser
    130                 135                 140

Ala Asp Ser Lys Pro Ile Asp Val Ser Arg Leu Asp Leu Arg Ile Gly
145                 150                 155                 160

Cys Ile Ile Thr Ala Arg Lys His Pro Asp Ala Asp Ser Leu Tyr Val
                165                 170                 175

Glu Glu Val Asp Val Gly Glu Ile Ala Pro Arg Thr Val Val Ser Gly
                180                 185                 190

Leu Val Asn His Val Pro Leu Glu Gln Met Gln Asn Arg Met Val Ile
            195                 200                 205

Leu Leu Cys Asn Leu Lys Pro Ala Lys Met Arg Gly Val Leu Ser Gln
    210                 215                 220

Ala Met Val Met Cys Ala Ser Ser Pro Glu Lys Ile Glu Ile Leu Ala
225                 230                 235                 240

Pro Pro Asn Gly Ser Val Pro Gly Asp Arg Ile Thr Phe Asp Ala Phe
                245                 250                 255

Pro Gly Glu Pro Asp Lys Glu Leu Asn Pro Lys Lys Lys Ile Trp Glu
                260                 265                 270

Gln Ile Gln Pro Asp Leu His Thr Asn Asp Glu Cys Val Ala Thr Tyr
            275                 280                 285

Lys Gly Val Pro Phe Glu Val Lys Gly Lys Gly Val Cys Arg Ala Gln
    290                 295                 300

Thr Met Ser Asn Ser Gly Ile Lys
305                 310
```